United States Patent [19]

Bergentz et al.

[11] Patent Number: 4,729,766

[45] Date of Patent: Mar. 8, 1988

[54] VASCULAR PROSTHESIS AND METHOD IN PRODUCING IT

[75] Inventors: Sven E. Bergentz, Malmö; Kjell Bockasten; Kurt Strid, both of Lund, all of Sweden

[73] Assignee: Astra Meditec Aktiebolag, Molndal, Sweden

[21] Appl. No.: 725,153

[22] Filed: Apr. 22, 1985

Related U.S. Application Data

[63] Continuation of Ser. No. 583,489, Feb. 29, 1984, abandoned, which is a continuation of Ser. No. 295,362, Aug. 24, 1981, abandoned.

[30] Foreign Application Priority Data

Aug. 28, 1980 [SE] Sweden ................... 8006024

[51] Int. Cl.⁴ .................. A61F 2/04; B23K 27/00
[52] U.S. Cl. .................. 623/1; 128/1 R; 219/121 LJ
[58] Field of Search .......... 3/1, 1.4; 128/1 R; 623/1, 10, 11, 16, 17; 219/121 LJ, 121 LE, 121 LF, 121 LH

[56] References Cited

U.S. PATENT DOCUMENTS

| | | | |
|---|---|---|---|
| 3,105,492 | 10/1963 | Jeckel | 3/1.4 X |
| 3,700,380 | 10/1972 | Kitrilakis | |
| 3,914,802 | 10/1975 | Reick | |
| 4,070,514 | 1/1978 | Eatherly et al. | |
| 4,073,999 | 2/1978 | Bryan et al. | |
| 4,170,726 | 10/1979 | Okuda | 219/121 LJ |
| 4,250,372 | 2/1981 | Tari | 219/121 LS |
| 4,280,500 | 7/1981 | Ono | 128/DIG. 21 |
| 4,301,816 | 11/1981 | Wahle et al. | 131/88 |
| 4,304,010 | 12/1981 | Mano | 3/1.4 |
| 4,321,711 | 3/1982 | Mano | 3/1.4 |
| 4,322,600 | 3/1982 | Crahay | 219/121 LS |
| 4,338,508 | 7/1982 | Jones et al. | 219/121 LS |
| 4,377,736 | 3/1983 | Daunt et al. | 219/121 LH |

FOREIGN PATENT DOCUMENTS

| | | | |
|---|---|---|---|
| 2149027 | 4/1972 | Fed. Rep. of Germany | 3/1.4 |
| 2811591 | 9/1979 | Fed. Rep. of Germany | 3/1.4 |
| 71129530 | 10/1974 | Sweden | |
| 1367918 | 10/1974 | United Kingdom | |
| 1371624 | 10/1974 | United Kingdom | |
| 1436054 | 5/1976 | United Kingdom | |
| 1552388 | 9/1979 | United Kingdom | 623/1 |
| 2029308 | 3/1980 | United Kingdom | |

Primary Examiner—Richard J. Apley
Assistant Examiner—David J. Isabella
Attorney, Agent, or Firm—Brumbaugh, Graves, Donohue & Raymond

[57] ABSTRACT

The invention relates to a vascular prosthesis in the form of a flexible tube which can be implanted in animals or human beings, with a regular pattern of blind holes in the external surface of the tube, which are regular with regard to direction, transverse dimensions and depth and are produced by laser treatment.

The invention also relates to a method of producing such a vascular prosthesis consisting in that the holes are produced by means of pulsated laser beams along one or more helical lines, the tube being rotated and displaced axially at the same time.

10 Claims, 17 Drawing Figures

VASCULAR PROSTHESIS AND METHOD IN PRODUCING IT

This application is a continuation of application Ser. No. 583,489, filed on Feb. 29, 1984, which is a continuation of application Ser. No. 295,362, filed on Aug. 24, 1981, both now abandoned.

The invention relates to a vascular prosthesis in the form of a flexible tube which can be implanted in animals or human beings, wherein at least one outer surface layer consists of a soft synthetic material with microdepressions in the external surface of the tube.

Further, the invention relates to a method for producing a vascular prosthesis of this kind.

It is an indispensible requirement that such a vascular prosthesis should be able to fulfil for a long tim, i.e. for several years, its vitally important function in the organism in which it is implanted. This presupposes that the vascular prosthesis is of a material which is not rejected by the organism and which has such mechanical properties that the vascular prosthesis can withstand the varying internal pressures to which it may be exposed, that it can bend with a small radius without becoming occluded and that it can be firmly sewn to joining blood vessels, producing a satisfactory anastomosis, without the suture thread cutting through the material. The lumen must be bounded by a surface which does not tend to give rise the thrombosis and thromboembolisms, and the external surface of the vascular prosthesis should be compatible with tissue and allow the prosthesis to be anchored by the tissue growing or infiltrating into the wall of the vessel so that no oedema is formed or inflammation occurs through displacement or twisting of the vascular prosthesis in relation to adjacent tissues. Furthermore, it is necessary for the material in the vascular prosthesis to be able to stand some form of sterilization. Finally, it should be added that the properties listed above must be present at the temperature at which the vascular prosthesis is to be used, namely, at body temperature.

The vascular prosthesis which has been used for the longest time consists of porous textile material, usually a crimped or resiliently circular-knitted stocking of polymerized ethyleneglycolterephthalate (Dacron). It also occurs in embodiments with a velour covering on the outside or both on the outside and the inside to promote the growing of the surrounding tissue into the implanted vascular prosthesis, even into the boundary surface of the lumen, so that a pseudointimal coating is obtained on the boundary surface, which is more resistant to blood coagulation than the actual surface of the vascular prosthesis. Deposits of fibrin and cellular material from the blood also contribute to the formation of this coating. In this manner, the vascular prosthesis is covered internally, within a few days, with a biological lining which can be tolerated by the blood and prevents the occurrence of thrombosis or thromboembolisms. The textile vascular prostheses must, however, be treated with blood, so-called preclotting, before they are implanted, which involves a time-consuming and lengthy pre-treatment. The textile vascular prostheses are accepted by the organism and fulfil their function well if they have a limited length and a sufficiently large internal diameter and work with a rapid flow of blood and under high pressure. If these conditions are not fulfilled, the woven vascular prostheses have a short operative life.

In recent years, vascular prostheses have been made of expanded polytetrafluorethylene (Teflon) which forms a network of nodes and flexible fibrils. The advantage of this type of vascular prosthesis is above all that it can be given the desired porosity and the desired flexibility and that no pretreatment with blood is necessary. Moreover, it is easy to suture and is resistant to occlusion. A substantial disadvantage, however, is that the vascular prosthesis has an uneven surface at the inside and cannot be heparinized to prevent particles in the blood from coating the inside of the vascular prosthesis. It is still too early to judge whether this type of vascular prosthesis is better, with regard to its operation, than the vascular prosthesis of textile material.

According to the German laid open specification 2,149,027 it has been proposed to produce microdepressions in the external surface of an implant by a procedure wherein particles, granulate or fibres of predetermined size and shape are embedded into the material of the external surface of the implant and are then removed again so that depressions remain in the surface, which correspond to the size and shape of the particles, granulate or fibres at the embedding locations. The method produces a random distribution of the depressions, and certain parts of the surface may be supplied to a lesser extent than others. It is mentioned in the specification that the implant may be in the form of a vascular prosthesis but it does not appear to have reached any practical use as such, probably because the microdepressions produced in the manner indicated do not permit a satisfactory growing-in of surrounding tissue to achieve a reliable anchoring of a vascular prosthesis in the organism.

The invention is a contribution to the efforts made in order to provide a vascular prosthesis which satisfies the requirements discussed above.

The vascular prosthesis of the kind initially referred to, which has been provided according to the invention, has obtained the features which appear from claim 1. This vascular prosthesis has a non-permeable wall, which is an important difference from the vascular prostheses now used of a permeable construction. No pre-clotting is therefore required.

The vascular prosthesis preferably consists of polyurethane with blind holes set obliquely to the radial direction alternately in one direction and the other. Then, in a particularly advantageous manner the holes may be inter-connected in pairs at their inner ends, so that they form a duct from the surface of the vascular prosthesis which extends through the material of the vascular prosthesis and then goes out again to emerge at the surface of the vascular prosthesis In order that the vascular prosthesis can be sutured more easily and reliably when connected to adjacent blood vessels, it is a further advantage to reinforce the wall of the vascular prosthesis with a stocking of textile material embedded in the material.

Embodiments of the invention will be described in more detail below together with a method of producing the vascular prosthesis, reference being made to the accompanying drawings in which.

Figure 1:
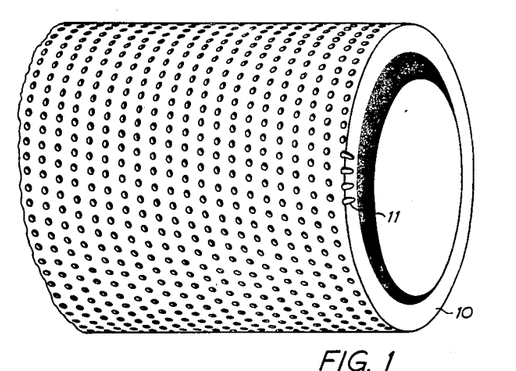
FIG. 1 is a greatly enlarged perspective view of a part of a vascular prosthesis according to the invention.
Figures 2, 3, 5, 6:
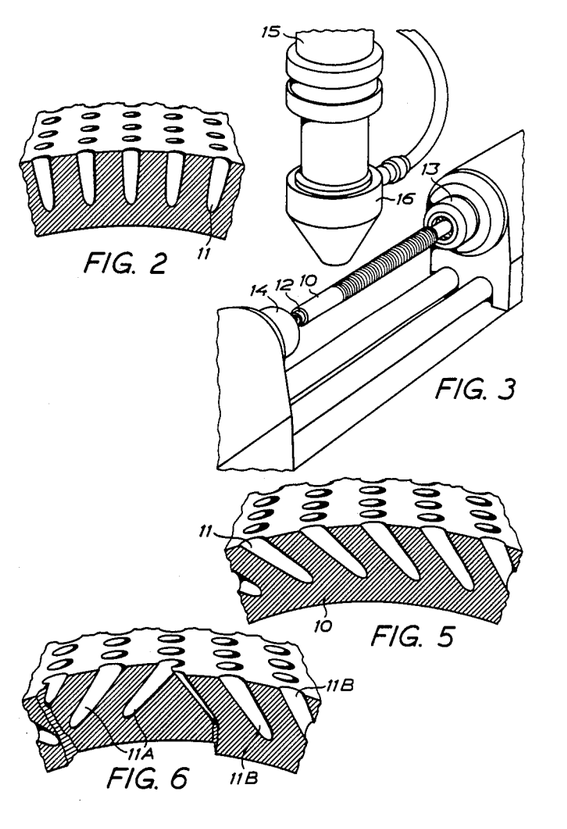
FIG. 2 is a further enlarged fragmentary perspective sectional view of the vascular prosthesis in FIG. 1.
FIG. 3 is a perspective view of a simple laboratory apparatus for producing blind holes in the external surface of the vascular prosthesis as shown in FIGS. 1 and 2.
FIG. 5 is a view corresponding to FIG. 2 of yet another embodiment of the invention.
FIG. 6 is a view corresponding to FIG. 2 of a still further embodiment of the invention.

With reference to FIGS. 1 and 2, the vascular prosthesis according to the invention shown therein consists of a moulded, injection-moulded or extruded cylindrical, flexible tube 10 of a synthetic material, for example a plastic, preferably polyurethane, which is compatible with tissue and is available in various degrees of hardness. In order to obtain a good connection to the body's own blood vessels at the anastomosis the material should be soft. Shore numbers of 20° to 25° have proved suitable. In itself, this material has a negative electrical surface charge, which is an advantage, as mentioned in the introduction, since the material repels thrombocytes as a result thereof. However, materials which do not have such a negative electrical surface charge, for example polyvinylacetate, can also be used in the vascular prosthesis according to the invention, if they are suitable for heparinizing, i.e. the incorporation of heparin in the vessel wall at the inside of the tube. As a result of the heparinizing, the inside becomes repellant to thrombocytes and particles in the blood are prevented from coating the inside of the vascular prosthesis, and so the occurrence of thromboses and thromoembolisms is prevented. Even materials which already have a negative surface charge can be heparinized at the inside of the tube if it is desired to increase the thrombocyte-repelling effect. Polyethylene, polytetrafluorethylene and silicone rubber may be mentioned as further examples of materials which are suitable for the vascular prosthesis according to the invention. On the other hand, polyvinyl chloride for example, is unsuitable, since it changes during the laser treatment. The changes are manifested by discolouring of the material. Materials which undergo structural changes during laser treatment, which are manifested as carbonization of the surface or discolouration of the material, should not be used for the vascular prosthesis according to the invention.

Summing up, it is required of the material which is used for the vascular prosthesis, that it should be accepted by the organism and should not be rejected by the organism after the implantation, and that it should have a negative electrical surface charge or be able to be heparinized. Furthermore, the material should be able to be treated with a laser without undergoing structural changes, and it should have such mechanical properties that it can withstand the stresses to which it is exposed not only during manufacture but also when the vascular prosthesis is implanted in the organism. The material should be soft so that the vascular prosthesis can bend with a small radius without a tendency to so-called cracking. The fact that the material is soft is also a prerequisite for the vascular prosthesis to seal against joining blood vessels, which have often grown stiff due to calcification, during the connection to these blood vessels. At the same time, however, the material should afford adequate securing means for the suture thread which should not tend to cut through the material. As will be shown later, in connection with another embodiment of the invention, the anchoring of the suture thread can, however, be improved by inserting a reinforcement in the tube wall. Finally, it is, of course, necessary for the material of the vascular prosthesis to be able to stand some form of sterilization, for example beta or gamma sterilization. It may be added that the properties listed must be present at the temperature at which the vascular prosthesis is to be used, namely at body temperature.

In order that the vascular prosthesis may be able to fulfil its purpose, it must be able to be anchored in the body by the growing-in and infiltration of the tissue into the wall of the prosthesis to eliminate oedema and inflammation. In order that this growing-in may be uniform over the whole external surface of the vascular prosthesis, this is formed with a regular pattern of microdepressions in the form of blind holes, which may be interconnected as described above. It is an essential requirement that the whole surface should be uniformly provided with these holes. The holes are disposed substantially radially in the embodiment shown in FIGS. 1 and 2. The holes are produced by laser treatment which can be effected in the manner shown in FIG. 3. According to this figure, the tube 10 is passed onto a mandrel 12 which is secured between a chuck 13 and a tailstock 14. The chuck and the tailstock may constitute parts of a conventional lathe. Simultaneously with the rotation of the tube 10, axial displacement of the tube is brought about. A laser, partially indicated at 15, is placed with its focussing lens system 16 above the tube 10. The laser beam is directed radially towards the tube. While the tube is rotated and displaced axially, the laser is pulsated to produce a hole in the tube wall on each pulse, the holes thus formed coming to lie on a continuous helical line round the outside of the tube.

During the production of a vascular prosthesis of polyurethane with a hardness of 20° to 25° Shore, the tube was rotated with a pitch of 0.30 mm. The pulse frequency of the laser and the rate of rotation of the tube were selected so that the spacing between the holes along the helical line was about 0.30 mm. The laser used was a 500 W $CO_2$ laser with radiation in the form of a parallel beam of infrared light with a wavelength of 10.6 $\mu$m. The diameter of the beam was about 12 mm, and this beam was focussed by the lens 16 on the surface of the stock material. In order that well-defined holes may be obtained, though the tube is rotating at a constant speed, the pulse period must be selected so that it is short in comparison with the itnerval between two pulses; with a pulse rate of 100–400 pulses per second, the pulse period is of the order of 10–100 $\mu$s. With correct focussing of the laser beam on the tube, the hole diameter is 0.10 mm, but the hole diameter can be increased by defocussing slightly. The depth of hole is determined by the energy of the laser pulse, and this depth should appropriately be selected so that the distance from the bottom of the hole to the inner wall corresponds to approximately at least 25%, and preferably 30%–35%, of the thickness of the tube wall.

In an embodiment of a vascular prosthesis of polyurethane produced in this manner the hole diameter was 0.150 mm and the hole depth 0.30 mm with a wall thickness of 0.40 mm. The hole spacing was 0.30 mm and the pitch of the helical line 0.30 mm. There were about 11 holes on each square millimeter of the surface of the vascular prosthesis.

In another embodiment, the hole diameter was 0.125 mm and the hole depth again 0.30 mm with a wall thickness of 0.40 mm. The hole spacing was 0.25 mm and the pitch likewise 0.25 mm. This corresponds to 16 holes/mm$^2$.

The hole pattern which is obtained by the laser treatment is very regular and reproducible, since the pulse energy and pulse rate of the laser can be adjusted accurately. The number of holes per unit of surface can be altered by altering the pitch and the spacing between the holes along the helical line. The individual holes will be very regular. The method of producing microdepressions in this manner is clean and contact-free, since the material which is removed by means of the laser is gasified instantaneously and blown away. The treatment is carried out in an inert atmosphere by a stream of argon being blown towards the tube during the treatment.

Figure 4:
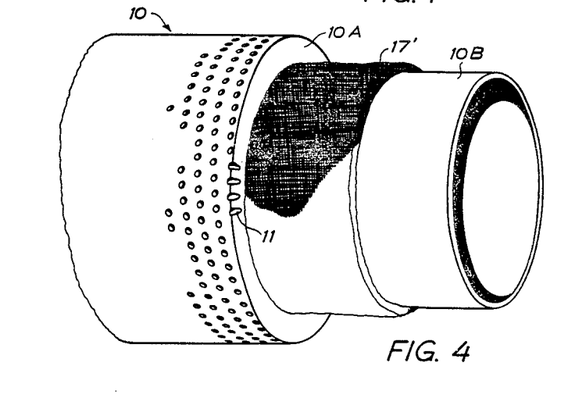
FIG. 4 is a perspective view, with parts broken away, of a vascular prosthesis as shown in FIGS. 1 and 2, but with a reinforcing stocking of textile material embedded in the wall of the vascular prosthesis.

FIG. 4 shows a vascular prosthesis with holes 11 arranged in the same manner as in FIGS. 1 and 2. Embedded in the tube wall, however, is a circularknitted stocking 17' of textile material, preferably of Dacron, so that the tube has a portion 10A at the outside of the stocking, in which the holes 11 are provided, and an internal portion 10B at the inside of the stocking, which forms the interior of the vascular prosthesis. The stocking 17' serves to bring about the anchoring of the suture during the connection of the vascular prosthesis, so that it is not necessary to rely only on the material of the tube for the anchoring of the suture, and eliminates the risk of the suture cutting through this material. The stocking 17' can be laid in the material in the tube during the moulding, injection molding or extrusion thereof. This embodiment is also interesting from the point of view that the tube can be produced of a composite material, meaning that the portion 10A is of a material different from that of the portion 10B. In this manner, a material can be selected for the portion 10A which is suitable for laser treatment and for growing-in and infiltration of surrounding tissue, while a material can be selected for the portion 10B which is suitable to form the lumen of the vascular prosthesis, i.e. a material without a tendency to form thromboses or thromboembolisms.

In the embodiments shown in FIGS. 1, 2 and 4, the holes 11 are disposed radially, i.e. they are at right angles to the external surface of the vascular prosthesis and to its longitudinal axis. The laser may, however, be directed obliquely to the external surface of the vascular prosthesis but still in a plane which is at right angles to the longitudinal axis of the tube 10, and in such a case the holes 11 are set obliquely as shown in FIG. 5. A suitable inclination to the radial direction is of the order of 45°. As a result of the inclination of the holes, these can be made longer at unaltered wall thickness and an unaltered spacing between the inner ends of the holes and the boundary surface of the lumen. The inclination and the increased length of the blind holes afford a better anchoring of the vascular prosthesis during the growing-in of surrounding tissue into the implanted vascular prosthesis.

Figure 7:
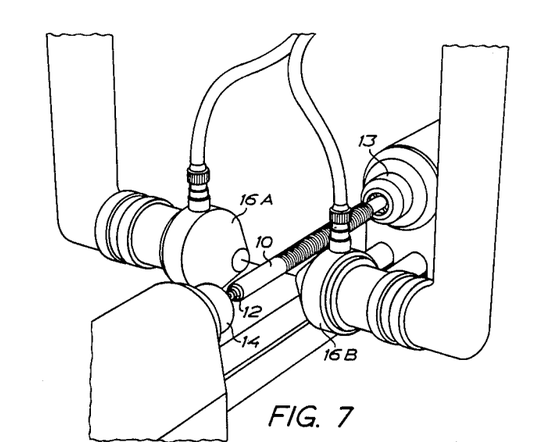
FIG. 7 is a perspective view of an apparatus for producing the vascular prosthesis as shown in FIG. 6.
Figure 8:
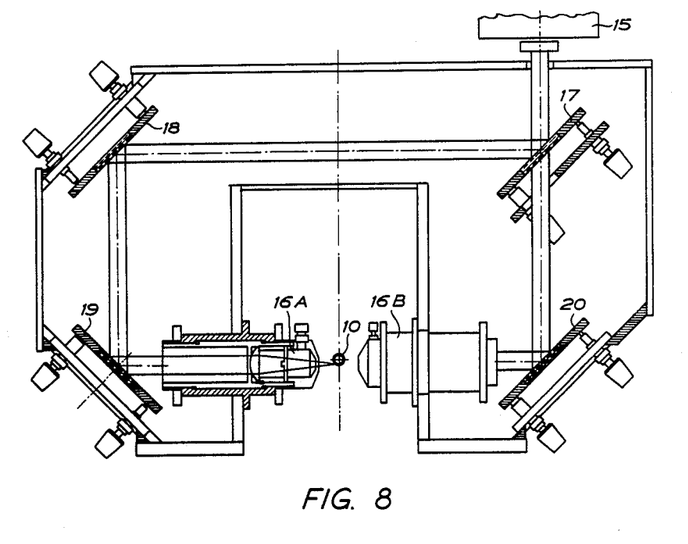
FIG. 8 is a diagrammatic view, which shows the construction of the apparatus in FIG. 7.
Figure 9:
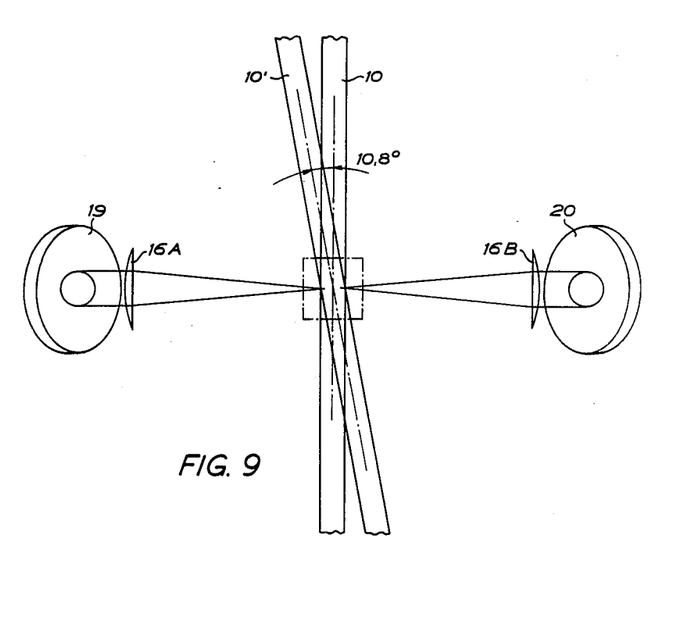
FIG. 9 is a diagrammatic plan view which shows the geometric relationships during the production of a vascular prosthesis in the apparatus shown in FIG. 7.

FIG. 6, to which reference is now made, illustrates a further development of the embodiment as shown in FIG. 5, according to which the blind holes are inclined alternately to one side and the other but still extend in planes which are at right angles to the longitudinal axis of the tube. Holes 11A are situated on a helical line with a pitch of 0.60 mm substantially at 45° to the radial direction, i.e. substantially at 45° to the external surface of the tube, while holes 11B are disposed on another helical line with a pitch of 0.60 mm but offset axially by 0.30 mm in relation to the first helical line. These holes also form an angle of substantially 45° to the radial direction of the tube but are inclined in the opposite direction to the holes 11A. All the holes have their axes in planes which are at right angles to the longitudinal axis of the tube. Thus, in two adjacent rows of holes, the holes are directed obliquely in opposite directions, and this system of holes can be produced during a single feed of the tube if the laser beam is divided into two beams of equal intensity by means of a beam splitter. Figures 7–9 illustrate method and apparatus for producing the hole pattern as shown in FIG. 6.

Figure 10:
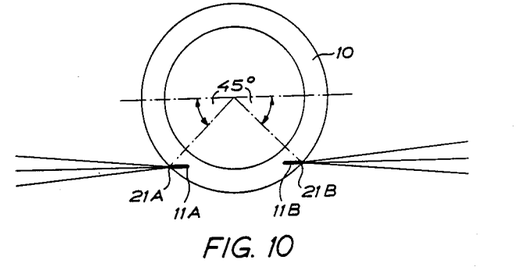
FIG. 10 is a diagrammatic cross-sectional view, which likewise illustrates the geometric relationships during the production of a vascular prosthesis in the apparatus shown in FIG. 7.

With reference mainly to FIG. 8, the beam of light from the laser 15 is directed towards a semitransparent mirror 17 at an angle of 45°, and the divided beam is transmitted further on the one hand via two mirrors 18 and 19 to a lens 16A and on the other hand via a mirror 20 to a lens 16B. As can be seen also from FIG. 7, the lenses 16A and 16B are situated at opposite sides of the tube 10 set up in the lathe to direct their beams towards the tube from opposite directions. This is also illustrated in FIGS. 9 and 10, and as can best be seen from FIG. 10, the beams impinge on the tube below the axis at the points 21A and 21B, which are offset by 45° from the horizontal plane, to produce the holes 11A and 11B, respectively.

Figure 11:
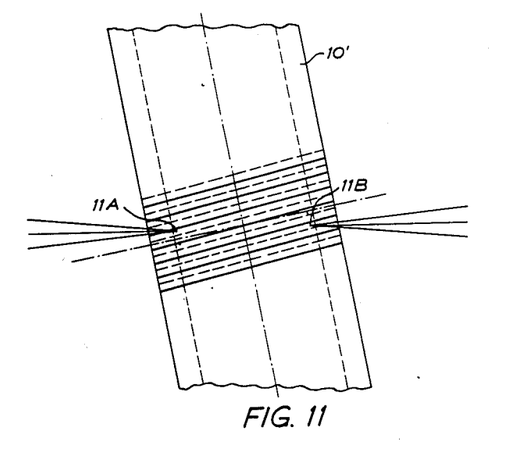
FIG. 11 is an enlarged part of the plan view in FIG. 9; namely the part which is marked by a square in chain line.
Figure 12:
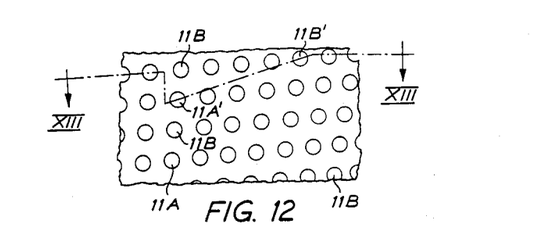
FIG. 12 is a fragmentary plan view of the external surface of a vascular prosthesis according to the invention in yet another modified embodiment.
Figure 13:
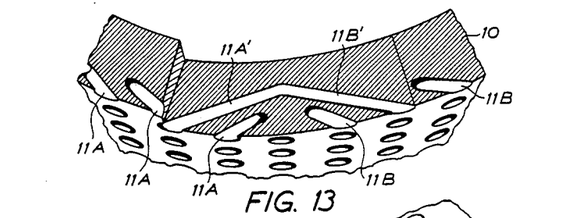
FIG. 13 is a sectional view on the line XIII—XIII in FIG. 12.
Figure 14:
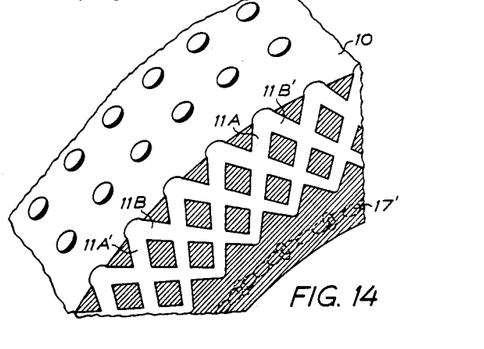
FIG. 14 is a greatly enlarged fragmentary perspective view of a further embodiment of the vascular prosthesis according to the invention.

As a result of the fact that the tube 10 is inclined in relation to the position in FIG. 9, where the beams from the lenses are perpendicular to the tube axis, so that the tube assumes the position 10', FIG. 9, the holes no longer come to lie with their axes in planes which are at right angles to the longitudinal axis of the tube. This can be seen more clearly from FIG. 11. A hole 11A on one helical line can therefore be brought to join at the bottom thereof, the bottom of a hole 11B on the other helical line, so that together the holes form a duct which enters the tube wall from its outside at one point and comes out again at another point on the outside of the tube wall. This is illustrated in FIGS. 12 and 13 where the holes 11A' and 11B' are shown connected to one another. The holes 11A' and 11B' are still termed blind holes inasmuch as they do not extend through the wall thickness, notwithstanding that they are interconnected at their inner ends and may cut through other holes (FIG. 14). From FIGS. 12 and 13 it will be apparent that there are 3 holes in the peripheral direction between the two connected holes, which are situated one in each of two rows of holes located beside one another in the axial direction. As a result of this arrangement, the anchoring of the implanted vascular prosthesis in the surrounding tissue can be further considerably improved by the growing-in and infiltration of the tissue in the holes. It is, of course, conceivable to allow the holes to be connected otherwise than as shown in FIG. 12. The fact that the connected holes cut through other adjacent holes does not matter in itself. In other words, by disposing the holes as shown in FIGS. 12 and 13, it is possible to achieve that the surface layer of the vascular prosthesis acquires the character of a porous material with communicating cells. It is desirable that the surface layer should be as porous as possible without jeopardizing the strength.

In the embodiment shown in FIG. 14, the holes disposed on one and the same helical line are connected to one another, a hole 11A substantially at an angle of 45° to the external surface of the tube communicating at its inner end with another hole 11B which is situated on the same helical line as the hole 11A and is directed substantially at an angle of 45° to the external surface of the tube but is inclined in the opposite direction to the hole 11A. Thus, the holes 11A and 11B meet at their inner ends substantially at a right angle. The hole 11A has its mouth at the external surface of the tube in common with another hole 11B', inclined in the opposite direction to the hole 11A, and the hole 11B has its mouth on the external surfce of the tube in common with another hole 11A' inclined in the opposite direction to the hole 11B. Between each pair of holes which communicate with one another at the inner ends, there lie two hole mouths, and each hole cuts through two holes which originate from these mouths. In FIG. 14, the tube wall has a reinforcing stocking 17'.

Figure 15:
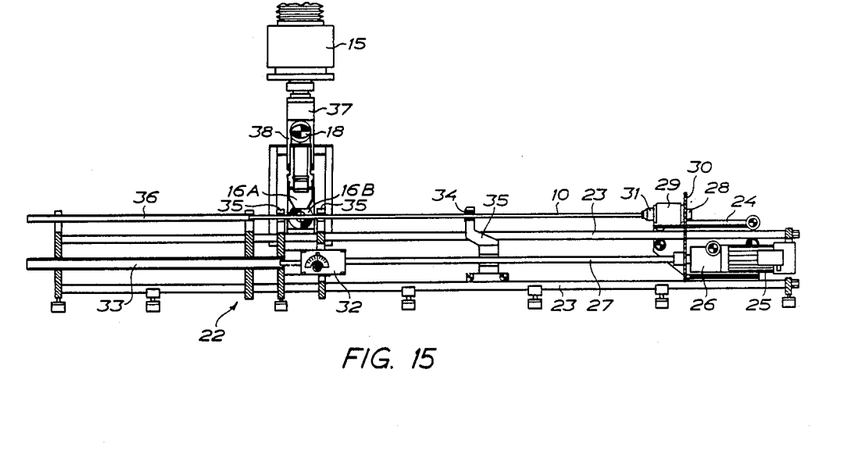
FIG. 15 is a side view of an apparatus for producing the vascular prosthesis according to the invention, adjusted to produce the embodiment as shown in FIG. 14.
Figures 16, 17:
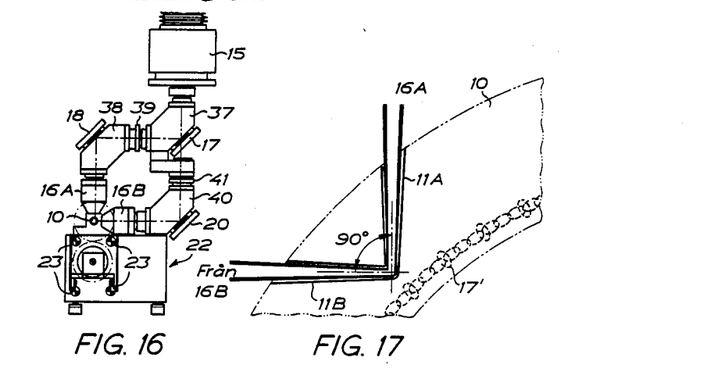
FIG. 16 is an end view of the apparatus in FIG. 15.
FIG. 17 is a diagrammatic cross-sectional view; which illustrates how the laser beams are directed during the production of the vascular prosthesis as shown in FIG. 14 in the apparatus shown in FIGS. 15 and 16.

The apparatus shown in FIGS. 15 and 16 is set up for the production of the embodiment as shown in FIG. 14 but can also be used for the production of other described embodiments of the vascular prosthesis according to the invention. It comprises an elongated stand 22 with parallel guide bars 23 on which a carriage 24 is guided for displacement. Mounted on this carriage is an electric motor 25 with a change speed gear 26 to the output shaft of which there is coupled a shaft 27 which extends parallel to the guide bars 23 and can be rotated by means of the motor at an accurately adjusted rate of rotation. The output shaft of the change speed gear is also coupled to a shaft 28 which is parallel to the shaft 27 and is mounted in a headstock 29 mounted on the carriage, by means of a play-free transmission 30 with the ratio 1:1; this transmission may consist, for example, of a so-called Daimler-Benz gear. Mounted on the shaft 28 is a chuck 31 for securing the tube 10 which is to form the vascular prosthesis and which is passed onto a mandrel.

Fixedly mounted in the stand 22 is a linear feeder 32, the bar 27 being engaged therewith. By the rotation of the bar, this linear feeder causes an axial displacement of the bar accurately adjusted to the speed of rotation, and the linear feeder which is adjustable with regard to the relationship between speed of rotation and displacement. On axial displacement of the shaft to the left with regard to FIG. 15, during the rotation of the shaft, the shaft is taken up in a protective tube 33 which is disposed in the stand in parallel to the guide bars 23.

The tube 10 extends through a guide bushing 34 which is disposed on a carriage 35 which can travel freely on the guide bars 23. This carriage is initially placed substantially in the middle between the change speed gear 26 and the linear feeder 32. The shaft 27 passes freely through the carriage. Two fixed guide bushings 35 are also disposed on the stand. When the shaft 27 is rotated and at the same time is displaced axially, the carriage 24 is pulled towards the left displacing the tube 10 axially through the guide bushings 34 and 35 into a guide tube 36 which is fixedly mounted in the stand in parallel to the guide bars 23, the tube 10 being rotated at the same time and at the same speed as the shaft 27 via the transmission 30.

A laser of the kind indicated earlier, partially indicated at 15, is stationarily mounted associated with the stand 22. The bundle of rays from the laser is directed towards a semi-transparent mirror 17 at an angle of 45°, and the divided beam is transmitted further on the one hand via a mirror 18 to a lens 16A and on the other hand via a mirror 20 to a lens 16B. The lenses are adapted to direct their beams towards the tube 10 set up in the apparatus at an angle of 90° to one another; see FIG. 17. The mirror 17 is disposed in a unit 37 which is mounted on the laser 15, while the mirror 18 and the lens 16A are disposed in a unit 38 which is connected to the unit 37 by means of a rotary coupling 39, and the mirror 20 and the lens 16B are disposed in a unit 40 which is connected to the unit 37 by means of a rotary coupling 41 so that it is possible to direct the laser beams in various directions towards the tube 10. For the production of the vascular prosthesis as shown in FIG. 14, the laser beams are directed radially towards the tube to produce holes on a helical line when the laser is pulsated with simultaneous rotation and axial displacement of the tube 10 on rotation of the motor 25.

The guide bushing 34 provides a support for the tube so that it does not hang down or shake during the treatment. The carriage 25 gradually entrains the carriage 35 in its movement.

Various modifications are possible within the scope of the invention nd the invention, is not limited to the specific embodiments shown in the drawings. For example, the outer surface of the vascular prosthesis can be covered with holes in a much more dense pattern than that illustrated in the drawings, and even so densely that the entrances of adjacent holes partly overlaps each other. Further, it is possible to cover the surface with holes having rather a conical shape, that is that the diameter of the holes is gradually decreasing inwards. Such holes are easily obtained by suitable focusation of the lense system of the laser. With regard to possible coatings on the inside of the prosthesis one may, as a supplement or alternative to possible heparinization, provide the prosthesis with a thin hydrophilic coating containing e.g. polyvinylpyrrolidone or other innocuous hydrophilic polymers known to prevent the formation of blood-clots and giving a slippery surface with low frictional resistance against water-based liquids such as blood. Methods for obtaining such hydrophilic coatings are known in connection with production of catheters; see e.g. German laid open specification No. 2,828,617.

We claim:

1. A method of producing a vascular prosthesis comprising
   (1) mounting a tube of a biologically acceptable resinous material in relation to a laser means producing two focused beams directed to the outer surface of said tube from opposite sides thereof, whereby said tube and said laser means can move rotationally relative to each other around the longitudinal axis of said tube, and transversely relative to each other parallel to the longitudinal axis of said tube;
   (2) moving said tube rotationally relative to said laser means and simultaneously moving said tube axially relative to said laser means whereby the focus of light from said laser means traces a helical pattern on the surface of said tube;
   (3) focusing pulsed beams of light from said laser on the surface of said tube during said rotation; and
   (4) controlling the energy of each pulse and directing the beams to form microdepressions in the surface of said tube, the depth of which are not more than about 75% of the thickness of the wall of the tube, and wherein the microdepressions formed by the two laser beams intersect within the wall of the vascular prosthesis, thereby forming an interconnected hole which extends from one position on the external surface of the tube, and concurrently controlling the frequency of said pulses relative to the rotational and axial movement of the tube in relation to the laser beams such that the pulsed beams form a regularly spaced helical array of microdepressions in the surface of said tube.

2. A method according to claim 1, wherein one of the laser beams is directed radially toward said tube.

3. The method according to claim 1, wherein the pulse rate of the laser beams relative to the rotational and axial speed of the laser means in relation to the tube which forms the vascular prosthesis is such that the spacing of the holes formed by the laser beams is in the range of about 9 to 16 holes per square millimeter.

4. A method according to claim 1, wherein the focusing of the laser beams are controlled such that the microdepression formed by each pulse has a diameter in the range of about 50 to 200 micrometers.

5. A method according to claim 4, wherein the microdepressions formed by said laser beams are in the range of approximately 100 micrometers in diameter.

6. A method according to claim 1, wherein the wall thickness of the tube is in the range of about 0.75 to 1.0 millimeters.

7. The method according to claim 1, wherein said tube is of a material having a negative electrical charge on its surface, or has been heparinized.

8. The method according to claim 1, wherein the tube is of a plastic material compatible with tissue having a softness of a Shore number between about 20° and 25°.

9. The method according to claim 1, wherein the tube is made of polyurethane.

10. A vascular prosthesis made in accordance with the method according to claim 1.

* * * * *